United States Patent [19]

Goldberg et al.

[11] Patent Number: 4,585,587

[45] Date of Patent: Apr. 29, 1986

[54] ANTIGENIC PEPTIDE COMPOUNDS

[75] Inventors: Erwin Goldberg, Evanston; Thomas E. Wheat, Chicago, both of Ill.

[73] Assignee: Northwestern University, Evanston, Ill.

[21] Appl. No.: 663,057

[22] Filed: Oct. 19, 1984

[51] Int. Cl.$^4$ ............................................. C07C 103/52
[52] U.S. Cl. ............................................. 260/112.5 R
[58] Field of Search ................................. 260/112.5 R

[56] References Cited

U.S. PATENT DOCUMENTS 4,290,944 9/1981 Goldberg ..................... 260/112.5 R
4,353,822 10/1982 Goldberg ..................... 260/112.5 R
4,392,997 7/1983 Goldberg ..................... 260/112.5 R Primary Examiner—Delbert R. Phillips

[57] ABSTRACT

The novel antigenic linear peptides of this invention comprise peptides of from 4 to 13 amino acids, which are characterized by containing the sequence valine-leucine-aspartic acid-methionine. These compounds correspond with the amino acids 231 to 243, or segments thereof including sequence 239-242 of mouse LDH-C$_4$. The coupounds have utility in vaccines for reducing the fertility of female mammals.

19 Claims, No Drawings

ANTIGENIC PEPTIDE COMPOUNDS

GRANT REFERENCE

This invention was developed in part under Grant HD 05863 by the National Institute of Health.

BACKGROUND AND PRIOR ART

Mammalian spermatozoa have been known to be antigenic for many years. More recently, it has been demonstrated that mammalian sperm contain an antigenic enzyme, which is known as the $C_4$ isozyme of lactate dehydrogenase, (LDH-$C_4$). LDH-$C_4$ has been isolated in pure crystalline form from mouse testes. Goldberg (1972) *J. Biol. Chem.* 247:2044-2048. The enzyme has a molecular weight of 140,000 and is composed of four identical C subunits. The amino acid sequence and three-dimensional structure of LDH-$C_4$ have been studied-described by a number of investigators: Musick, et al., (1976) *J. Mol. Biol.* 104: 659-668; Wheat, et al., (1977) *Biochem & Biophys. Res. Comm.* 74, No. 3:1066-1077; Li, et al., (1983) *J. Biol. Chem.* 258:7017-7028; and Pan, et al (1983) *J. Biol. Chem.* 258:7005-7016.

In 1974, Dr. Erwin Goldberg reviewed the effects of immunization with LDH-X (LDH-$C_4$) on fertility, and advanced the possibility that "by using a defined macromolecular constituent of sperm it becomes possible to elucidate its primary structure in terms of amino acid sequence, to map specifically the antigenic determinant(s) responsible for inducing infertility, and then to construct synthetic peptides containing these determinants. Possessing the capability for synthesizing a molecule with such properties, makes the immunological approach to fertility control feasible". *Karolinska Symposia on Research Methods in Reproductive Endrocrinology,* 7th Symposium: Immunological Approaches to Fertility Control, Geneva, 1974 202-222.

Subsequent investigations by Dr. Goldberg and his research associates have identified several amino acid sequences of mouse LDH-$C_4$ which in isolated form (e.g., as short chain peptides) bind to LDH-$C_4$ antiserum. Wheat, et al., (1981), in Rich, et al., *Peptides: Synthesis-Structure-Function, Proc. 7th Amer. Peptide Symp.,* pp. 557-560; and Gonzales-Prevatt, et al., (1982) *Mol. Immunol.* 19:1579-1585. Antigenic peptide compounds based on these sequences have been patented. See U.S. Pat. Nos. 4,290,944; 4,310,456; 4,353,822; 4,377,516; and 4,392,997.

These antigenic peptides are useful in preparing vaccines to reduce female fertility. Immunization of female mammals results in the development of circulating antibodies specific to LDH-$C_4$. These immunoglobulins reach the female reproductive tract as a transudate of serum. Kille, et al., (1977), *Biol. Reprod.* 20:863-871. Antibody in cervical mucus, uterine fluids, and oviducal fluids combines with LDH-$C_4$ on the sperm surface and impedes the progress of the male gamete, presumably by agglutination. Systemic immunization with LDH-$C_4$ markedly interferes with sperm transport in the female reproductive tract. Kille, et al., (1980) *J. Reprod. Immunol.* 2:15-21.

The current status of research on LDH-$C_4$ and antigenic peptides for use in female contraceptive vaccines are summarized in two recent publications by the Goldberg group: Goldberg, et al., (1983), *In Immunology of Reproduction,* Chapt. 22, p. 493-504; and Wheat, et al., (1983), In *Isozymes: Current Topics in Biological and Medical Research,* Vol. 7, p. 113-140.

The search for additional antigenic peptides containing antibody binding sequences of mouse LDH-$C_4$ has continued. While it is known that this isozyme contains multiple antigenic domains, there is no recognized basis for locating such domains nor for predicting their effectiveness for antibody binding or for generating antibodies capable of interfering with sperm transport in female mammals. The effectiveness of immunocontraception by this route probably depends upon sufficiently high concentrations of antibodies in the reproductive tract. To date, laboratory trial and error experimentation has been the only available approach.

SUMMARY OF INVENTION

A new class of antigenic peptide compounds binding to LDH-$C_4$ antisera has now been discovered. These short chain linear peptides includes the L-amino acid sequence of valine-leucine-aspartic acid-methionine, which is believed to comprise the minimal antigenic domain, which corresponds to amino acids MC 239-242 in mouse LDH-$C_4$, as sequenced by Li, et al., (1983) *J. Biol. Chem.* 258:7017-7028. The peptide compounds of this invention may include other amino acids of LDH-$C_4$ connecting with and including the antigenic domain. As will subsequently be described in detail, the class of peptides of this invention includes at least eighteen compounds. These compounds can be used to prepare vaccines for reducing the fertility of female mammals including woman, since mouse LDH-$C_4$ is homologous with human LDH-$C_4$.

DETAILED DESCRIPTION

Standard abbreviations and symbols will be used herein to designate the amino acid present in the peptide compounds of this invention. These are:

| Amino Acids | Abbreviations | Symbols |
| --- | --- | --- |
| L-aspartic acid | Asp | D |
| L-glutamic acid | Glu | E |
| L-glutamine | Gln | Q |
| glycine | Gly | G |
| L-leucine | Leu | L |
| L-lysine | Lys | K |
| L-methionine | Met | M |
| L-tyrosine | Tyr | Y |
| L-valine | Val | V |

The antigenic peptide compounds of this invention comprise the class of compounds corresponding to the amino acid sequence MC 231 to 243 of mouse LDH-$C_4$ or segments thereof including MC 239-242. More specifically the class of peptides include the following:

(a) Q-V-V-E-G-G-Y-E-V-L-D-M-K,
(b) Q-V-V-E-G-G-Y-E-V-L-D-M,
(c) V-V-E-G-G-Y-E-V-L-D-M-K,
(d) V-V-E-G-G-Y-E-V-L-D-M,
(e) V-E-G-G-Y-E-V-L-D-M-K,
(f) V-E-G-G-Y-E-V-L-D-M,
(g) E-G-G-Y-E-V-L-D-M-K,
(h) E-G-G-Y-E-V-L-D-M,
(i) G-G-Y-E-V-L-D-M-K,
(j) G-G-Y-E-V-L-D-M,
(k) G-Y-E-V-L-D-M-K,
(l) G-Y-E-V-L-D-M,
(m) Y-E-V-L-D-M-K,
(n) Y-E-V-L-D-M, (o) E-V-L-D-M-K,
(p) E-V-L-D-M,
(q) V-L-D-M-K, and
(r) V-L-D-M.

The above formulas represent linear peptides shown in left to right representation, the N-terminal amino acid being on the left end and the C-terminal amino acid being on the right end. All of the amino acids represented are L-amino acids with the exception of glycine (G) which has not L and D forms.

The peptide compounds of the present invention can be synthesized from their constituent amino acids. For example, the synthesis can be carried out by the Merrifield solid phase method, as described in *J.A.C.S.* 85:2149–2154 (1963). This solid phase method for synthesizing sequences of amino acids is also described in Stewart and Young, *Solid Phase Peptide Synthesis* (W. H. Freeman and Co., San Francisco, 1969), pages 1–4. In this procedure, the C-terminal amino acid is attached to chloromethylated polystyrene-divinylbenzene copolymer beads. Each subsequent amino acid, with suitable protecting group, is then added sequentially to the growing chain. For example, as described in the Merrifield article, the protective group may be a carbobenzoxy group. By the procedure of coupling, deprotection, and coupling of the next amino acid, the desired amino acid sequence and chain length can be produced. As a final step, the protective group is removed from the N-terminal amino acid (viz., lysine and the C-terminal amino acid is cleaved from the resin, using a suitable reagent, such as trifluoroacetic acid and hydrogen bromide. Since this synthesis procedure is well known, it is not believed that it will be necessary to further describe it herein.

To utilize the antigenic peptides of this invention in the form of a fertility reducing vaccine, the peptide is conjugated to a carrier molecule, which is preferably a protein which itself elicits an antigenic response and which can be safely administered. For example, the peptide can be coupled to tetanus toxoid for administration by intramuscular injection. For example, a mixture of 1 μMole tetanus toxoid, 60 μMoles antigenic peptide, and 18 millimoles 1-ethyl-3-(3 dimethyl aminopropyl) carbodiimide hydrochloride reacted in water (pH6) for 12 hours at room temperature and 24 hours at 4° gives a product containing 3.5 moles of peptide/mole tetanus toxoid. Excess reactants can be removed by dialysis or gel filtration. See Pique et al., *Immunochemistry*, 15:55–60 (1978). Alternatively, the peptide may be coupled using bisdiazotized benzidine (Bassiri et al, *Endocrinology*, 90:722 (1972) or glutaraldehyde.

For intramuscular injection, the coupled peptide may be suspended in a sterile isotonic saline solution, or other conventional vehicle, and, if desired, an adjuvant may be included. A preferred use of such a vaccine is for administration to human females. Antibodies will be formed, which will appear in the oviduct fluids and thereby produce a significant reduction in fertility. For this purpose, the amount to be administered will range from about 1 to 10 milligrams (mg) of the antigenic peptide.

The compounds of this invention and their antigenic properties are further illustrated by the following examples.

EXAMPLE I

The purification of peptides by reverse phase high performance liquid chromatography has been described by Wheat, et al., (1981), cited above. Pure mouse LDH-$C_4$ is reduced and carboxymethylated with iodoacetic acid. Digestion with trypsin (4% w/w) proceeds for 4 hours in the presence of 2M urea. After desalting on Sephadex G-10, the digest is fractionated on a μBondapak $C_{18}$ column (3.9 mm × 30 cm; Waters Associates) with a gradient of increasing acetonitrile. Trifluoroacetic acid (0.04%) is present throughout the gradient. The column effluent is monitored at 214 nm, and fractions are collected manually based on peak absorbance. Fractions are dried under a stream of nitrogen and lyophilized from water. Purity is assessed isocratically in the same chromatographic system, and peptides are repurified as necessary. Following hydrolysis (6N HCl, 107°, 40 hrs.), amino acid compositions are determined with reverse phase chromatography of o-pthalaldehyde derivatives. See Hill, et al., (1979) *Anal. Chem.* 51:k338–1341. Amino acid sequences were established by the manual Edman degradation. See Tarr (1977) in *Methods in Enzymology*, Vol. 47, pp. 335–357; and Tarr (1981) *Anal. Biochem.* 111:27–32.

Following this procedure a segment was obtained which was later determined to be the sequence Gln-Val-Val-Glu-Gly-Gly-Tyr-Glu-Val-Leu-Asp-Met-Lys. The peptide was tested for antibody binding activity as follows:

Antibody binding by the purified peptide was assessed with a solid matrix radioimmunoassay. The peptide was coated on the walls of a polyvinyl chloride microtiter plate by incubating, overnight at 4° C., a solution containing 5 nmoles of peptide in 100 μl of 0.05 M $NaPO_4$, 0.14 M NaCl (PBS) in each well. Each well was washed with 200 μl/well 10% horse serum in PBS and incubated for 1 hour in the same solution. After washing, the plate was incubated with 50 μl of the gamma-globulin fraction of pooled rabbit antimouse LDH-$C_4$ sera. After 4-hours incubation, the plate was washed and then incubated with 100 μl/well of $^{125}$I-goat antirabbit gamma-globulin for 16 hours at 4° C. After exhaustive washing, bound radioactivity was determined using a gamma counter.

EXAMPLE II

Synthesis of the peptide Gln-Val-Val-Glu-Gly-Gly-Tyr-Glu-Val-Leu-Asp-Met-Lys can be carried out employing known solid phase techniques. In a preferred procedure amino protected lysine, representing the —COOH terminal group of the above peptide, is coupled to a conventional solid phase peptide synthesis resin such as chloromethyl polystyrene cross-linked with 1 to 2% divinyl benzene. The amino protecting group is then selectively removed utilizing a suitable reagent whose nature will depend on the protecting group used. In the preferred embodiment the t-butyloxycarbonyl (Boc) group is utilized for amino group protection and 40% trifluoroacetic acid in methylene chloride is the selective deprotecting agent.

After deprotection, the lysine is treated with protected methionine, preferably Boc-methionine, and dicyclohexylcarbodiimide in a manner known per se as to form a peptide bond between the free amino group of the lysine residue and the carboxyl group of protected methionine.

The cycle of deprotection and coupling with amino acid derivatives and dicyclohexylcarbodiimide is then repeated with the remaining amino acids in the sequence order of the above peptide. Some of the amino acids required side-chain blocking groups besides the alpha-amino protection. Such amino acids and the blocking groups are as follows:

Asp(oBzl) Lys(Z) Glu(oBzl) Tyr(Bzl) Glu(oNp)

where Np is nitrophenyl, Bzl is benzyl and Z is ε-carbobenzoxy.

Completion of the synthesis provided the following tridecapeptide coupled to the styrenedivinylbenzene copolymer resin:

Gln(oNp)Val-Val-Glu(oBzl)-Gly-Gly-Tyr(Bzl)-Glu(OBzl)-Val-Leu-Asp(oBzl)-Met-Lys(Z).

Decoupling of the peptide from the resin is accomplished by treatment with liquid hydrogen fluoride with concomitant cleavage of all protecting groups to produce the desired peptide, identified above as compound (a).

The other peptides of this invention, comprising compounds (b) to (r) as further identified above, are similarly synthesized. For example, for compound (g) the decapeptide coupled to resin will be:

Glu(oBzl)-Gly-Gly-Tyr(Bzl)-Glu(oBzl)-Val-Leu-Asp(oBzl)Met-Lys(Z).

For compound (r) the four amino acid peptide coupled to the resin will be:

Val-Leu-Asp(oBzl)-Met.

The antibody binding activity of the peptides, prepared as described, can be determined as described in Example I, and are useable in female contraceptive vaccines.

We claim:

1. Antigenic peptide compounds binding to LDH-C$_4$ antiserum, comprising the class of linear peptide compounds containing the antigenic domain V-L-D-M and being selected from the sequences of N-terminal to C-terminal amino acids represented by:

(a) Q-V-V-E-G-G-Y-E-V-L-D-M-K,
(b) Q-V-V-E-G-G-Y-E-V-L-D-M,
(c) V-V-E-G-G-Y-E-V-L-D-M-K,
(d) V-V-E-G-G-Y-E-V-L-D-M,
(e) V-E-G-G-Y-E-V-L-D-M-K,
(f) V-E-G-G-Y-E-V-L-D-M,
(g) E-G-G-Y-E-V-L-D-M-K,
(h) E-G-G-Y-E-V-L-D-M,
(i) G-G-Y-E-V-L-D-M-K,
(j) G-G-Y-E-V-L-D-M,
(k) G-Y-E-V-L-D-M-K,
(l) G-Y-E-V-L-D-M,
(m) Y-E-V-L-D-M-K,
(n) Y-E-V-L-D-M,
(o) E-V-L-D-M-K,
(p) E-V-L-D-M,
(q) V-L-D-M-K, and
(r) V-L-D-M.

wherein G represents glycine, and Q, V, E, Y, L, D, M, and K, respectively represent the L-amino acid forms of glutamine, valine, glutamic acid, tyrosine, leucine, aspartic acid, methionine, and lysine.

2. The peptide compound (a) of claim 1.
3. The peptide compound (b) of claim 1.
4. The peptide compound (c) of claim 1.
5. The peptide compound (d) of claim 1.
6. The peptide compound (e) of claim 1.
7. The peptide compound (f) of claim 1.
8. The peptide compound (g) of claim 1.
9. The peptide compound (h) of claim 1.
10. The peptide compound (i) of claim 1.
11. The peptide compound (j) of claim 1.
12. The peptide compound (k) of claim 1.
13. The peptide compound (l) of claim 1.
14. The peptide compound (m) of claim 1.
15. The peptide compound (n) of claim 1.
16. The peptide compound (o) of claim 1.
17. The peptide compound (p) of claim 1.
18. The peptide compound (q) of claim 1.
19. The peptide compound (r) of claim 1.

* * * * *